United States Patent [19]
de Coriolis et al.

[11] Patent Number: 5,674,250
[45] Date of Patent: Oct. 7, 1997

[54] ATRIAL DEFIBRILLATOR AND METHOD FOR PROVIDING ADAPTIVE CONTROL OF DEFIBRILLATOR OUTPUT VOLTAGE

[75] Inventors: Paul E. de Coriolis, Bellevue; Gregory M. Ayers, Redmond, both of Wash.

[73] Assignee: InControl, Inc., Redmond, Wash.

[21] Appl. No.: 641,100

[22] Filed: Apr. 29, 1996

[51] Int. Cl.$^6$ .................................................. A61N 1/39
[52] U.S. Cl. .................................................. 607/7
[58] Field of Search .................... 607/5, 7, 8, 28, 607/4

[56] References Cited

U.S. PATENT DOCUMENTS 5,395,373  3/1995  Ayers ............................................. 607/8
5,507,780  4/1996  Finch ............................................. 607/5
5,531,770  7/1996  Kroll et al. .................................... 607/8

*Primary Examiner*—Jeffrey R. Jastrzab
*Attorney, Agent, or Firm*—Richard O. Gray, Jr.

[57] ABSTRACT

An implantable atrial defibrillator provides adaptive output voltage control. An atrial cardiovertor is responsive to an atrial fibrillation detector for applying a cardioverting voltage having a magnitude to the atria of a heart when the atria are in need of cardioversion. A memory stores data associated with each such voltage application. A computation stage computes from the stored data a percentage of success which is compared to lower and upper limits. The output voltage is incremented or decrement based upon the comparison. The output voltage may further be maintained within a fixed preselected voltage range.

21 Claims, 2 Drawing Sheets

ATRIAL DEFIBRILLATOR AND METHOD FOR PROVIDING ADAPTIVE CONTROL OF DEFIBRILLATOR OUTPUT VOLTAGE

BACKGROUND OF THE INVENTION

The present invention generally relates to an atrial defibrillator for applying cardioverting electrical energy to the atria of a human heart in need of cardioversion. The present invention is more particularly directed to a fully automatic implantable atrial defibrillator which provides adaptive control of the defibrillator output voltage based upon data stored in memory following each cardioversion attempt.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well know in the art. This treatment is commonly referred to as synchronized cardioversion and, as its name implies, involves applying electrical defibrillating energy to the heart in synchronism with a detected ventricular electrical activation (R wave) of the heart. The treatment is very painful requiring sedation or general anesthesia and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide relief to patients suffering from occurrences of atrial fibrillation. Unfortunately, to the detriment of such patients, none of these atrial defibrillators have become a commercial reality.

Two such proposed defibrillators, although represented as being implantable, were not fully automatic, requiring human interaction for cardioverting or defibrillating the heart. Both of these proposed defibrillators require the patient to recognize the symptoms of atrial fibrillation, with one defibrillator requiring a visit to a physician to activate the defibrillator, and the other defibrillator requiring the patient to activate the defibrillator with an external magnet.

An improved implantable atrial defibrillator and lead system which is truly automatic is fully described in U.S. Pat. No. 5,282,837, which issued on Feb. 1, 1994, for ATRIAL DEFIBRILLATOR AND METHOD, and which patent is assigned to the assignee of the present invention and is incorporated herein by reference. As disclosed in the aforementioned referenced patent, the defibrillator includes an atrial fibrillation detector for detecting atrial fibrillation of the heart and a cardiovertor for delivering defibrillating or cardioverting electrical energy to the atria in synchronism with a ventricular electrical activation (R wave) of the heart. Hence, this defibrillator automatically detects and cardioverts atrial defibrillation. The referenced synchronization is important to prevent inducing ventricular fibrillation. Ventricular fibrillation is a fatal arrhythmia which can be caused by electrical energy being delivered to the heart at the wrong time in the cardiac cycle, such as during the T wave of the cycle.

Another atrial defibrillator and method which provides further improvements to the end of safely and automatically cardioverting atrial defibrillation is described in U.S. Pat. No. 5,207,219, which issued on May 4, 1993, for ATRIAL DEFIBRILLATOR AND METHOD FOR PROVIDING INTERVAL TIMING PRIOR TO CARDIOVERSION, and which patent is also assigned to the assignee of the present invention and incorporated herein by reference. As described in that patent, it has been observed that during episodes of atrial fibrillation, the cardiac rate may increase to a high rate. At high cardiac rates, the R wave of each cardiac cycle becomes closely spaced from the T wave of the immediately preceding cardiac cycle. This may lead to a condition known in the art as an "R on T" condition which is believed to contribute to induced ventricular fibrillation if the atria are cardioverted in synchronism with an R wave close to a T wave.

The atrial defibrillator and method described in U.S. Pat. No. 5,207,219 greatly reduces this risk by avoiding applying the cardioverting electrical energy to the atria at those instances when increased vulnerability to ventricular fibrillation may be present. This is accomplished by interval timing prior to applying the cardioverting or defibrillating electrical energy. The time interval between immediately successive R waves is timed and the cardioverting or defibrillating electrical energy is applied when a timed interval is greater than a preselected minimum interval. This provides protection for the increased vulnerability to ventricular fibrillation condition resulting from a high cardiac rate.

It has further been observed that, for each atrial defibrillation, a distinct relationship exists between the percentage of successful cardioversion versus applied voltage. For example, a given patient may have a ten percent (10%) chance of being successfully cardioverted with a cardioverting peak voltage of 180 volts and a fifty percent (50%) chance at a peak cardioverting voltage of 220 volts. Another patient may have only a five percent (5%) chance and a fifteen percent (15%) at the same respective voltages. Further, there are points along the percentage of success versus voltage curve wherein, for a not insignificant low end voltage range, there would be essentially no chance of successful cardioversion and for a not insignificant upper end voltage range there would be no change in percent success. Hence, applied voltages in either range represents a waste of precious battery power. In the low end range, power would be wasted because there would be little if any chance of successful cardioversion. The same is true in the upper end range wherein any voltage above that which first results in no increase in percent of success represents wasted energy.

Applying a peak voltage to the atria of the heart of a patient which is in the upper range also imposes unnecessary discomfort to the patient. Since atrial fibrillation, unlike ventricular fibrillation, is not immediately life threatening, there is no reason to subject the patient to a voltage shock which would overly assure success. Rather, an applied lower voltage which may be easily tolerated by the patient would be better, even if more than one application may be necessary to achieve successful cardioversion. Hence, operating in a middle voltage range which bring less than one hundred percent (100%) chance of success but more than a limited success of twenty-five percent (25%), for example, may be of overall benefit to the patient both in terms of patient tolerance and device longevity.

Still, the percentage of success versus applied voltage relationship may change over time. Such may result due to changes in medication, changes in atria size, or other conditions. These considerations only complicate the manner in which effective, efficient, and tolerable therapy may be provided to a patient.

SUMMARY OF THE INVENTION

The invention provides an implantable atrial defibrillator including an atrial fibrillation detector and an atrial cardiovertor responsive to the atrial fibrillation detector for applying a cardioverting voltage to atria of a heart when the atria are in fibrillation, wherein the applied cardioverting voltage has a magnitude. The atrial defibrillator further includes a memory for storing data associated with each application of cardioverting voltage having the magnitude, analyzing means for analyzing the data, and varying means for varying the cardioverting voltage magnitude responsive to the analyzing means.

In accordance with a preferred embodiment, a data generator generates percentage of success data for each applied cardioverting voltage magnitude and a transmitter transmits the percentage of success cardioversion data to an external receiver. Also, the cardioverting voltage may be maintained within a predetermined range.

The present invention further provides a method of adjusting the cardioverting voltage magnitude of an implantable atrial defibrillator including the steps of applying a cardioverting voltage to the atria of the heart when the atria are in need of cardioversion wherein the applied cardioverting voltage has a magnitude, storing, in memory, data associated with each application of cardioverting voltage having the magnitude, analyzing the data, and varying the magnitude based upon the analysis.

The present invention still further provides an implantable atrial defibrillator including an atrial cardiovertor for applying electrical energy to atria of a heart when the atria are in need of cardioverison to attempt cardioversion of the atria, an atrial arrhythmia detector for determining success of a cardioversion attempt, means for increasing applied electrical energy based upon an unsuccessful cardioversion attempt, and means for decreasing applied electrical energy based upon a successful cardioversion attempt.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
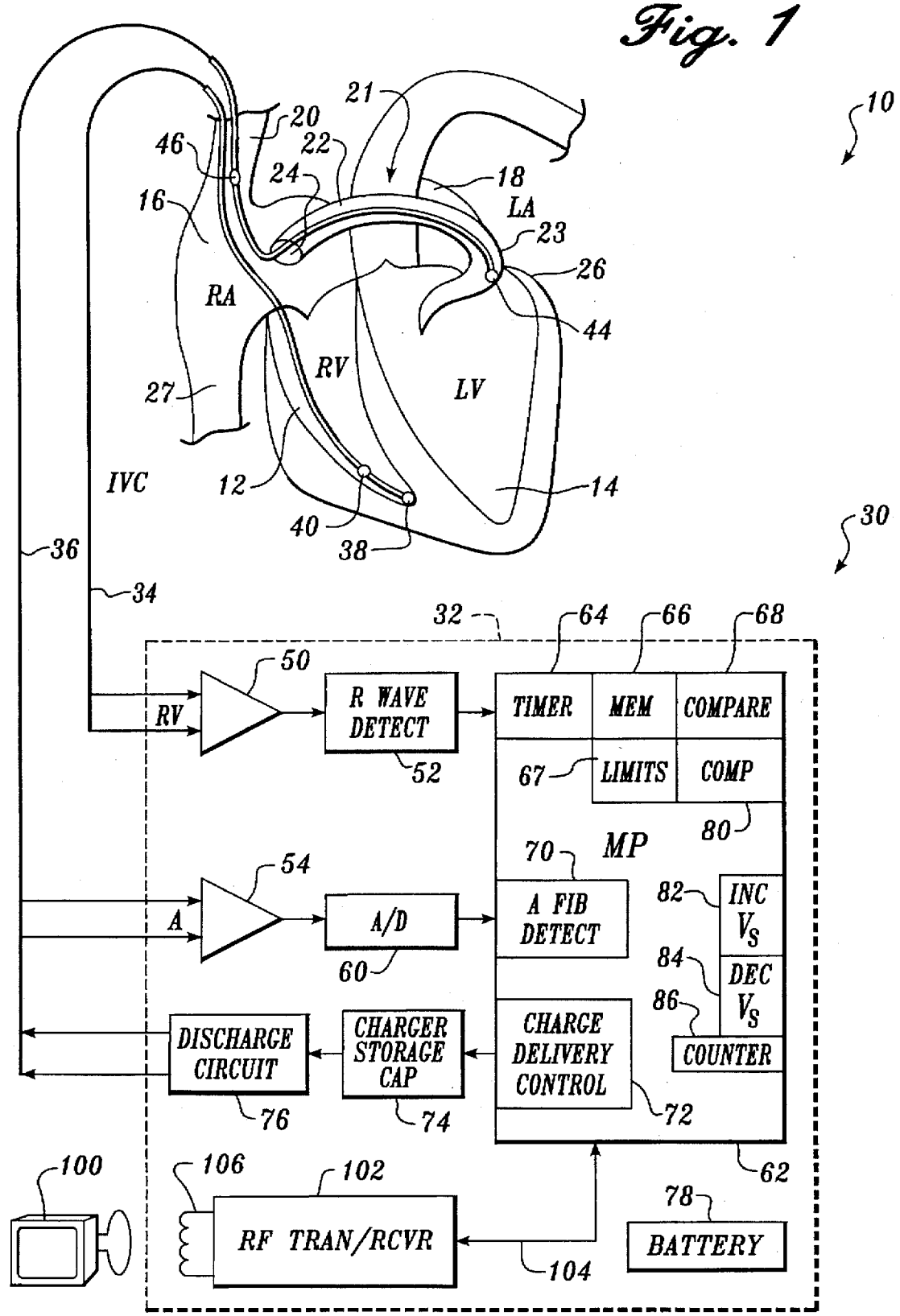
FIG. 1 is a schematic block diagram of a fully implantable atrial defibrillator embodying the present invention for applying cardioverting electrical energy to the atria of the heart and providing adaptive control of cardioversion output voltage.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23', the coronary sinus ostium or opening 24, the left ventricular free wall 26 and the inferior vena cava 27. In addition, as used herein, the term "ventricular activations" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is preferably fed through the superior vena cava 20, into the right atrium 16, and then into the right ventricle 12 as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21, either within the coronary sinus 22 adjacent the left ventricle 14 and beneath the left atrium 18, or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10.

Within the enclosure 32, the atrial defibrillator 30 includes a first sense amplifier 50, an R wave detector 52, and a second sense amplifier 54. The first sense amplifier 50 and the R wave detector 52 form a first detecting means which, together with the first lead 34 to which sense amplifier 50 is coupled, senses ventricular activations of the right ventricle 12. The second sense amplifier 54 forms a second detecting means which, together with the first electrode 44 and second electrode 46 of the second lead 36 to which it is coupled, detects atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart. The output of the second sense amplifier 54 is coupled to an analog to digital converter 60 which converts the analog signal representative of the atrial activity of the heart being detected to digital samples for further processing in a manner to be described hereinafter.

The enclosure 32 of the atrial defibrillator 30 further includes a microprocessor 62. The microprocessor 62 is preferably implemented in a manner as will be described hereinafter with respect to the flow diagram of FIG. 2 for providing automatic adaptive control of the output voltage of the defibrillator 30. The implementation of the microprocessor 62 in accordance with this embodiment of the present invention results in a plurality of functional stages. The stages include a timer 64, an internal memory 66, a comparator stage 68, an atrial arrhythmia detector in the form of an atrial fibrillation detector 70, a charge delivery and energy control stage 72, a computation stage 80, a shock voltage increment stage 82, a shock voltage decrement stage 84, and a counter 86.

The microprocessor 62 is arranged to operate in conjunction with an external memory (not shown) which may be coupled to the microprocessor 62 by a multiple-bit address bus (not shown) and a bi-directional multiple-bit data bus (not shown). This permits the microprocessor 62 to address desired memory locations within the memory for executing write or read operations. During a write operation, the microprocessor stores data, such as time intervals, or operating parameters in the memory at the addresses defined by multiple-bit addresses conveyed over the address bus and conveys the data to the memory 92 over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters such as percent of success or applied voltage limits or the like into the microprocessor 62, the microprocessor 62 receives the programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programmable operating parameters from the external controller 100 which the receiver/transmitter 102 then conveys to the microprocessor 62 for storage in internal memory 66, a memory portion 67, or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32.

To complete the identification of the various structural elements within the enclosure 32, the atrial defibrillator 30 further includes a charger and storage capacitor circuit 74 of the type well known in the art which charges a storage capacitor to a predetermined voltage level and a discharge circuit 76 for discharging the storage capacitor within circuit 74 for a predetermined discharge time to provide a controlled discharge output of electrical energy when required to the atria of the heart. To that end, the discharge circuit 76 is coupled to the first electrode 44 and the second electrode 46 of the second lead 36 for applying the cardioverting or defibrillating electrical energy to the atria. Lastly, the defibrillator 30 includes a depletable power source such as a lithium battery, for providing power to the electrical components of the atrial defibrillator 30.

If the atrial fibrillation detector 70 determines from the digital samples provided by the analog to digital converter 60 that the atria 16 and 18 are in fibrillation and thus in need of cardioversion, the charge delivery control 72 causes the charger and storage capacitor circuit 74 to charge the storage capacitor within circuit 74 to a desired voltage having a desired magnitude.

After the capacitor of circuit 74 is charged to the desired magnitude, the timer 64 times the time intervals between R waves of the heart. When timer 64 times a heart interval which is longer than the preselected minimum time interval, the charge delivery control 72 causes the discharge circuit 76 to discharge the capacitor of circuit 74 for a fixed period of time to apply the cardioverting electrical energy to electrodes 44 and 46 and thus the atria in timed relation to the R wave ending the last timed interval.

After each attempted cardioversion, the atrial fibrillation detector 70 determines if the cardioversion attempt was successful. If the attempt was not successful and the atria are still in fibrillation, the counter 86 is incremented and the defibrillator repeats the therapy at the same voltage.

Figure 2:
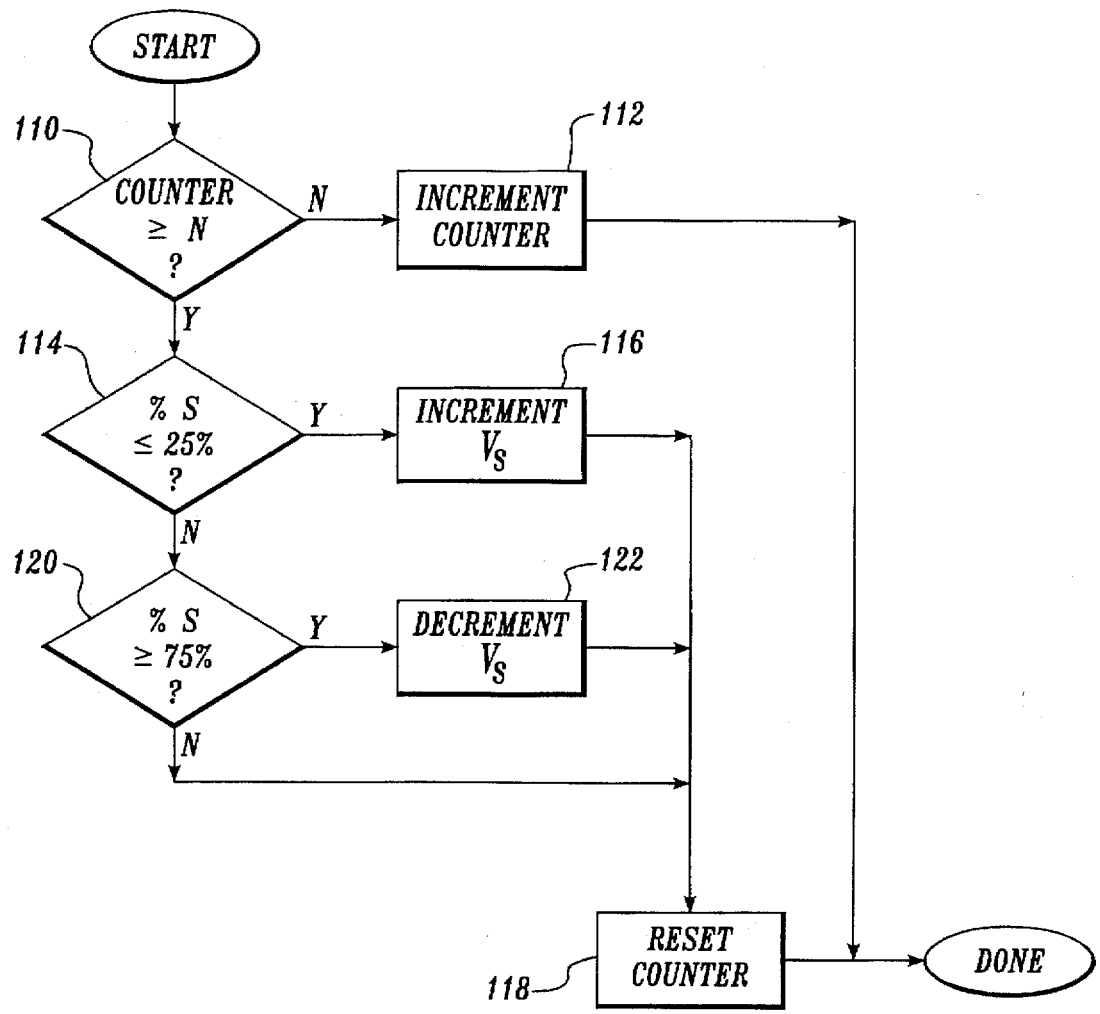
FIG. 2 is a flow diagram illustrating the manner in which the atrial defibrillator of FIG. 1 may be implemented in accordance with a preferred embodiment of the present invention.

If the attempted cardioversion was successful and the heart is now in normal sinus rhythm, counter 86 is incremented, an indicia is stored in memory 66 to denote a successful attempt at the current voltage level and the microprocessor 62 of the defibrillator 30, in accordance with this preferred embodiment, enters the subroutine of FIG. 2 to which reference is now made. The subroutine starts at step 110 wherein the counter 86 is interrogated to determine if it has counted a number of attempted cardioversions at the current voltage magnitude equal to or greater than some preset number such as ten, for example. This assures that further analysis will be based upon sufficient data to provide a statistically accurate result. If there have been less than N number of cardioversion attempts at the current voltage magnitude, the counter 86 is incremented at step 112 and the subroutine returns.

If there have been at least N number of attempts at the current shock voltage setting, the percentage of successful cardioversion is then computed by the computation stage 80. If, for example, five attempts were successful out of a total of ten attempts, the percentage of success at the current shock voltage would be fifty percent (50%).

Next, at step 114, the compare stage 68 determines if the percentage of success (S) at the current voltage is below a predetermined range having a lower limit of, for example, twenty-five percent (25%). If S is equal to or less than the lower limit, the shock voltage incrementing stage 82 incrementally increases the voltage output setting of the defibrillator at step 116. The capacitor of circuit 74, for the next attempt, will now be charged to an incrementally increased voltage before being discharged. This is to increase the percentage of success for this patient. The voltage increments may be any desired increment, for example ten (10) volts. Following step 116, the counter 86 is reset to zero in step 118.

If the percentage of success (S) is not less than the lower limit as determined in step 114, the compare stage 68 next in step 120 determines if S is equal to or greater than an upper limit of, for example, seventy-five percent (75%). If it is, the shock voltage decrementing stage 84, in step 122, decrements the output voltage setting of the defibrillator 30 by an amount, such as ten (10) volts, to decrease the percentage of success. Now, for the next cardioversion attempt, the capacitor of circuit 74 will be charged to a voltage which is ten (10) volts less than the voltage used in the immediately preceding attempt.

Hence, from the foregoing, it can be seen that, over time, the output voltage of the defibrillator will be adaptively adjusted to maintain a percentage of success within a desired range. This will assure that the battery power of the implanted defibrillator is efficiently utilized and that the patient is not being subject to more voltage than reasonably necessary.

Another feature of the present invention is in the generation of data representing a true percent of success versus voltage relationship- Each percent of success calculated by the computation stage 80 may be stored in memory 66 together with its corresponding output voltage. That data may then be transmitted to an external receiver, such as programmer 100, for use by the physician during patient follow-up.

Further, to assist the physician in patient follow-up, the percentage of success versus applied voltage may be plotted on a curve tracer or otherwise displayed to permit the physician to select an applied voltage range defined by a minimum permitted applied voltage and a maximum permitted applied voltage. The applied voltage range preferably over rides any voltage selection based upon percentage of success versus voltage. This may be especially important if the percentage of success versus voltage changes over time.

The minimum and maximum permitted applied voltages may be stored in a memory portion 67 dedicated to that function and the microprocessor may be programmed to prevent any output voltage increment or decrement which would cause the applied voltage to transition out of the physician prescribed range.

Also, the present invention may further find particular utility in a defibrillator which provides different output voltage levels during therapy intervention. Hence, after each cardioversion attempt, the output voltage magnitude is stored together with an indicia of success or failure and the total number of attempts at that voltage. In this way, the voltage levels may be adjusted or the sequence changed based upon percent of success to maximize a given factor.

The present invention may find further application wherein the magnitude of peak cardioversion voltage for a next attempted cardioverison may be based upon the magnitude of peak cardioversion voltage for a current attempt ($Vs_n$). More specifically, if a current attempt is unsuccessful, the voltage may be increased by a fixed increment (I) for the next attempt ($Vs_{n+1}=Vs_n+I$). However, if the current attempt is successful, the voltage may then be decreased by a fixed decrement (D) for the next attempt ($Vs_{n+1}=Vs_n-D$).

The above implementation has a number of characteristics. First, it seeks a target percent success which is a function of I/(I+D). The peak cardioversion voltage hunts or oscillates around the target percent success. The amplitude of the oscillations is a function of the maximum (I,D) and the slope of the dose-response curve at the target percent success. Lastly, only one data parameter (Vsn) need be temporarily stored or otherwise maintained for each attempted cardioversion.

While a particular embodiment of the invention has been shown and described, modification can be made, and it is therefore intended to cover in the appended claims all such changes and modifications which fall within the true spirit and scope of the invention.

What is claimed is:

1. An implantable atrial defibrillator comprising:
   an atrial fibrillation detector for detecting spontaneous episodes of atrial fibrillation;
   an atrial cardioverter responsive to each detected spontaneous episode of atrial fibrillation for applying a cardioverting voltage to atria of a heart, the applied cardioverting voltage having a magnitude;
   a memory for storing accumulated data associated with a plurality of applications of cardioverting voltage having the magnitude;
   analyzing means for analyzing the accumulated data; and
   varying means for varying the cardioverting voltage magnitude responsive to the analyzing means.

2. An atrial defibrillator as defined in claim 1 wherein the analyzing means includes means for computing a percentage of successful cardioversions for a given magnitude of cardioverting voltage.

3. An atrial defibrillator as defined in claim 2 wherein the analyzing means includes compare means for determining if the percentage of success falls within a predetermined percentage of success range.

4. An atrial defibrillator as defined in claim 3 further including incrementing means for increasing the cardioverting voltage magnitude if the percentage of success is below the range.

5. An atrial defibrillator as defined in claim 3 further including decrementing means for decreasing the cardioverting voltage magnitude if the percentage of success is above the range.

6. An atrial defibrillator as defined in claim 1 further including means for generating percentage of successful cardioversions data for each applied cardioverting voltage magnitude.

7. An atrial defibrillator as defined in claim 6 further including transmitting means for transmitting the percentage of successful cardioversion data to an external receiver.

8. An atrial defibrillator as defined in claim 1 further including means for maintaining the cardioverting voltage magnitude below a predetermined maximum permitted cardioverting voltage magnitude.

9. An atrial defibrillator as defined in claim 1 further including means for maintaining the cardioverting voltage magnitude within a predetermined range.

10. In an implantable atrial defibrillator, a method of operating the defibrillator to adjust a cardioverting voltage magnitude comprising the steps of:
    detecting spontaneous episodes of atrial fibrillation;
    applying a cardioverting voltage to atria of a heart responsive to each detected spontaneous episode of atrial fibrillation, the applied cardioverting voltage having a magnitude;
    storing in a memory accumulated data associated with a plurality of applications of cardioverting voltage having the magnitude;
    analyzing the accumulated data to obtain results; and
    varying the magnitude based upon the results.

11. A method as defined in claim 10 including the further step of determining if the atria are not in need of cardioversion prior to the storing step.

12. A method as defined in claim 11 wherein the storing step includes storing the voltage magnitude and an indicia if the atria are not in need of cardioversion.

13. A method as defined in claim 12 wherein the storing step includes storing the number of applications of voltage to the atria at the voltage magnitude.

14. A method as defined in claim 13 wherein the analyzing step includes calculating the percentage of successful cardioversions at the voltage magnitude.

15. A method as defined in claim 14 wherein the varying step includes increasing the voltage magnitude if the percentage of success is below a predetermined percent of success range.

16. A method as defined in claim 15 wherein the varying step further includes decreasing the voltage magnitude if the percentage of success is above the range.

17. A method as defined in claim 10 wherein the storing step includes storing data representative of a percentage of successful cardioversions for each applied different voltage magnitude.

18. A method as defined in claim 17 including the further step of transmitting the stored data to an external receiver.

19. A method as defined in claim 10 including the further step of precluding the cardioverting voltage magnitude from exceeding a maximum permitted cardioverting voltage magnitude.

20. A method as defined in claim 10 including the further step of maintaining the cardioverting voltage magnitude within a permitted cardioverting voltage range.

21. An implantable atrial defibrillator comprising:
an atrial cardiovertor for applying electrical energy to atria of a heart when the atria are in need of cardioversion to attempt cardioversion of the atria;
an atrial arrhythmia detector for determining success of a cardioversion attempt;
means for increasing applied electrical energy based upon an unsuccessful cardioversion attempt; and
means for decreasing applied electrical energy based upon a successful cardioversion attempt.

* * * * *

UNITED STATES PATENT AND TRADEMARK OFFICE
CERTIFICATE OF CORRECTION

PATENT NO. : 5,674,250
DATED : October 7, 1997
INVENTOR(S) : Paul E. de Coriolis and Gregory M. Ayers It is certified that error appears in the above-identified patent and that said Letters Patent is hereby corrected as shown below:

| Column | Line | |
|--------|------|---|
| 4 | 8 | delete --'-- after "23" |
| 6 | 3 | insert --78,-- after "source" |

Signed and Sealed this

Twenty-fourth Day of March, 1998

Attest:

BRUCE LEHMAN

*Attesting Officer*  *Commissioner of Patents and Trademarks*